United States Patent [19]

Bugaut et al.

[11] 4,432,769
[45] Feb. 21, 1984

[54] NITRO DYESTUFFS, A PROCESS FOR THEIR PREPARATION, AND USE OF THESE DYESTUFFS IN DYEING KERATIN FIBRES

[75] Inventors: Andree Bugaut, Boulogne-Billancourt; Patrick Andrillon, Chelles, both of France

[73] Assignee: L'Oreal, Paris, France

[21] Appl. No.: 291,098

[22] Filed: Aug. 7, 1981

[30] Foreign Application Priority Data

Aug. 8, 1980 [FR] France ................. 80 17617

[51] Int. Cl.³ .............. A61K 7/13; C07C 89/00; C07C 91/06; C07C 93/14
[52] U.S. Cl. .................................. 8/414; 8/405; 8/407; 564/441
[58] Field of Search .............. 8/405, 407, 414; 564/441

[56] References Cited

U.S. PATENT DOCUMENTS 1,670,969  5/1928  Knecht .................. 564/441
3,930,792  1/1976  Alperin et al. ............ 8/414 X

FOREIGN PATENT DOCUMENTS 2195424   3/1974  France .
2290186   6/1977  France .
2349325  11/1977  France .
1520787   8/1978  United Kingdom .
1531605  11/1978  United Kingdom .

OTHER PUBLICATIONS

Ames et al., "Dyes are Mutagenic; Identification of a Variety of Mutagenic Ingredients", *Proc. Nat. Acad. Sci.,* USA, vol. 72, No. 6, pp. 2, 423-2, 427 (Jun. 1975).
Journal of the American Chemistry Society, vol. 64, Kremer et al., pp. 1285-1286, (Jun. 1942).
Chemical Abstracts, vol. 47: 1133i, (1953).
Chemical Abstracts, vol. 51: 5096i, (1957).

*Primary Examiner*—Natalie Trousof
*Assistant Examiner*—Vera C. Clarke
*Attorney, Agent, or Firm*—Fleit, Jacobson, Cohn & Price

[57] ABSTRACT

Compounds having the general formula:

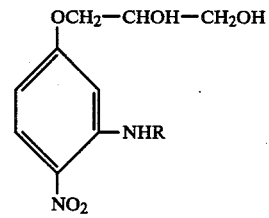

in which R denotes hydrogen, a lower alkyl, lower hydroxyalkyl or lower polyhydroxyalkyl radical or alternatively an alkyl, hydroxyalkyl or polyhydroxyalkyl radical in which the alkyl chain is interrupted by one or more hetero-atoms such as oxygen are described. These compounds can be used in dyeing compositions for keratin fibres and wavesetting lotions. They make it possible to obtain very strong shades.

35 Claims, No Drawings

NITRO DYESTUFFS, A PROCESS FOR THEIR PREPARATION, AND USE OF THESE DYESTUFFS IN DYEING KERATIN FIBRES

DESCRIPTION

The present invention relates to new nitro dyestuffs which can be used in dyeing keratin fibres and in particular human hair.

Ether derivatives of 4-nitro-3-aminophenols are already known and are described, in particular, in French Pat. Nos. 2,290,186 and 2,349,325.

However, although these known ethers possess valuable properties in hair dyeing, they do not possess sufficient solubility in an aqueous-alcoholic mixture and do not make it possible to obtain very strong shades in hair dyeing.

We have therefore carried out further research and have discovered that it is possible to overcome these disadvantages by using the compounds of the general formula:

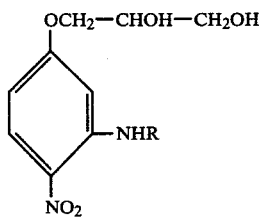

in which R denotes hydrogen, a lower alkyl radical, preferably $C_1$ to $C_4$, a lower hydroxyalkyl radical, preferably $C_2$ to $C_6$, or a lower polyhydroxyalkyl radical, preferably $C_3$ to $C_6$, or alternatively an alkyl, hydroxyalkyl or polyhydroxyalkyl radical in which the alkyl chain is interrupted by one or more hetero-atoms such as oxygen, this alkyl chain preferably having 3 to 8 carbon atoms.

The term "lower alkyl (hydroxyalkyl or polyhydroxyalkyl) radical" is to be understood as meaning a $C_1$ to $C_6$ radical.

The preferred lower alkyl radicals are, in particular, methyl, ethyl, propyl or butyl radicals.

Preferred lower hydroxyalkyl radicals which may be mentioned in particular are the β-hydroxyethyl and β-hydroxypropyl radicals and the preferred polyhydroxyalkyl radical which may be mentioned in particular is the β,γ-dihydroxypropyl radical.

The compounds of formula (I) are in fact much more soluble in aqueous-alcoholic solution than the known compounds, and make it possible to obtain much stronger hair colourations having a considerably greater chromaticity than that of ethers derived from 4-nitro-3-aminophenols, described in French Pat. Nos. 2,290,186 and 2,349,325.

It will be recalled that the chromaticity is designated by C in Munsell's notation, according to which a colour is defined by the notation:

HV/C in which the three parameters respectively denote the shade or "hue" (H), the intensity or "value" (V) and the purity or "chromaticity" (C), the oblique line being a simple convention.

For further details of Munsell's notation, reference may be made to the publication "Official Digest", April 1964, pages 373 to 377.

We have also discovered that the nitro dyestuffs of the above formula (I) possess the very valuable property of being substantially non-mutagenic.

The non-mutagenic character of these dyestuffs can be assessed with the aid of the Ames test on *Salmonella typhimurium*, with or without S9 mix, activated or non-activated by Arochlor (prior treatment of the rats with Arochlor), and this is carried out on the five strains TA 1535, TA 1537, TA 100, TA 1538 and TA 98.

As regards the Ames test, reference may be made to the following literature: B. N. AMES, H. O. KAMMEN and E. YAMASAKI, "Dyes are mutagenic; Identification of a variety of mutagenic ingredients", Proc. Nat. Acad. Sci. USA, Volume 72, No. 6, pages 2,423–2,427 (June 1975); and B. N. AMES, J. McCANN and E. YAMASAKI, "Methods for detecting carcinogens and mutagens with Salmonella mammalian microsome mutagenicity test", Mutation Res., 31 (1975), pages 347–364.

The present invention thus provides the chemical compounds of formula (I), and also a process for their preparation.

The present invention also provides dyeing compositions for keratin fibres and in particular for human hair, containing the compounds of formula (I), and to a process for treating the hair, using the said compositions.

Amongst the compounds of formula (I) according to the invention, particularly preferred compounds are: 3-amino-4-nitrophenyl β,γ-dihydroxypropyl ether, 3-N-methylamino-4-nitrophenyl β,γ-dihydroxypropyl ether, 3-N-butylamino-4-nitrophenyl β, γ-dihydroxypropyl ether, 3-N-(β-hydroxyethyl)-amino-4-nitrophenyl β,γ-dihydroxypropyl ether, 3-N-(β-hydroxypropyl)-amino-4-nitrophenyl β,γ-dihydroxypropyl ether and 3-N-(β,γ-dihydroxypropyl)amino-4-nitrophenyl β,γ-dihydroxypropyl ether.

These compounds possess very good solubility in an aqueous-alcoholic mixture.

Moreover, the use of these dyestuffs in hair dyeing makes it possible to obtain very strong, yellow colourations of high chromaticity, which can be as much as 12, for example, in the case of 3-N-methylamino-4-nitrophenyl β,γ-dihydroxypropyl ether used at its solubility limit in an aqueous-alcoholic solution, for dyeing hair which has been bleached white.

The compounds of formula (I) can be prepared from 3-amino-4-nitro-chlorobenzene or its derivatives of formula (II), in which R has the meaning already indicated, in accordance with the following equation:

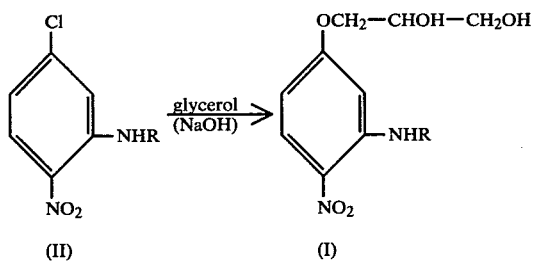

Typically, glycerol in which sodium hydroxide is dissolved beforehand is reacted with 3-amino-4-nitro-chlorobenzene or a derivative thereof of formula (II), at 100°–150° C., whilst stirring. The product (I) can subsequently be isolated and then optionally recrystallised.

The compounds of formula (II) can be prepared from 2,4-dichloro-nitrobenzene by selective substitution of the chlorine atom ortho to the nitro group by an amine $RNH_2$, under sufficiently mild conditions for the substitution to be selective.

The dyeing compositions according to the invention contain at least one compound of formula (I) in an aqueous, alcohol or aqueous-alcoholic vehicle.

The concentration of the compounds of formula (I) in the dyeing compositions according to the invention is suitably 0.001 to 5% by weight and preferably 0.01 to 3% by weight, relative to the total weight of the dyeing composition.

The pH of the dyeing compositions according to the invention is suitably from 3 to 11.5 and preferably from 5 to 11.5. It can be adjusted to the desired value with the aid of an alkalising agent such as ammonia, sodium carbonate, potassium carbonate or ammonium carbonate, sodium hydroxide or potassium hydroxide, an alkanolamine such as mono-, di- or tri-ethanolamine, or an alkylamine such as ethylamine or triethylamine, or with the aid of an acidifying agent such as phosphoric, hydrochloric, tartaric, acetic, lactic or citric acid.

The compositions according to the invention can also contain other direct dyestuffs such as azo or anthraquinone dyestuffs, nitro benzene dyestuffs, indoanilines, indophenols, indamines, or hydroxynaphthoquinones such as juglone (5-hydroxy-1,4-naphthoquinone) or lawsone (2-hydroxy-1,4-naphthoquinone).

The concentrations of these direct dyestuffs other than the dyestuffs of formula (I) is generally from 0.001 to 5% by weight, relative to the total weight of the composition.

The dyeing compositions according to the invention can also contain anionic, cationic, non-ionic or amphoteric surface-active agents or mixtures thereof.

The surface-active products are suitably present in the compositions according to the invention in proportions from 0.5 to 55% by weight and preferably of from 4 to 40% by weight, relative to the total weight of the composition.

Organic solvents can also be included in the compositions according to the invention in order to solubilise compounds which would not be sufficiently soluble in water. Amongst the solvents which can advantageously be used, examples which may be mentioned are lower alkanols such as ethanol and isopropanol, glycerol, glycols or glycol ethers, such as 2-butoxyethanol, ethylene glycol, ethylene glycol monoethyl ether, propylene glycol, and diethylene glycol monoethyl ether and monomethyl ether, as well as analogous products, and mixtures thereof. These solvents are preferably present in proportions from 1 to 75% by weight and more particularly from 5 to 50% by weight, relative to the total weight of the composition.

The compositions according to the invention can be thickened, preferably with compounds such as sodium alginate, gum arabic, cellulose derivatives such as methylcellulose, hydroxyethylcellulose, hydroxypropylmethylcellulose and carboxymethylcellulose, and various polymers acting as thickeners, in particular acrylic acid derivatives. It is also possible to use inorganic thickeners such as bentonite. These thickeners are preferably present in proportions of 0.5 to 10% by weight and in particular of 0.5 to 3% by weight, relative to the total weight of the composition.

The compositions according to the invention can also contain various adjuvants normally used in hair-dyeing compositions, and in particular penetrating agents, sequestering agents, film-forming agents, buffers and perfumes.

The dyeing compositions according to the invention can be presented in various forms such as liquids, creams or gels, or in any other form suitable for dyeing hair. They can also be packaged in aerosol flasks, in the presence of a propellant.

The compositions according to the invention, containing at least one compound of formula (I), can be used in a process for dyeing hair by direct colouration. These compositions are applied to the hair for, say, 5 to 40 minutes, this application being followed by rinsing, washing, if appropriate, and drying the hair.

The compositions according to the invention can also be used in the form of hair wavesetting lotions which are intended both to impart a slight colouration to the hair and to improve the hold of the set.

In this case, they are presented in the form of aqueous-alcoholic solutions containing at least one cosmetic resin, and they are generally applied to dump hair which has been washed and rinsed beforehand, and the hair is then wound onto rollers and dried.

The cosmetic resins used in the wavesetting lotions can be, in particular, polyvinylpyrrolidone and the following copolymers: crotonic acid/vinyl acetate, vinylpyrrolidone/vinyl acetate, maleic anhydride/butyl vinyl ether and maleic anhydride/methyl vinyl ether. These cosmetic resins are normally used in the compositions of the invention in an amount from 1 to 3% by weight and preferably 1 to 2% by weight, based on the total weight of the composition.

The compounds of formula (I) can also be used in oxidation dyeing compositions in accordance with a hair-dyeing process which involves developing by means of an oxidising agent.

In this case, the compositions according to the invention contain, in association with at least one nitro dyestuff of formula (I), an oxidation dyestuff precursors of the ortho or para type or a mixture thereof.

They can contain, for example, para-phenylenediamines such as: para-phenylenediamine, para-toluylenediamine, 2,6-dimethyl-para-phenylenediamine, 2,6-dimethyl-3-methoxy-para-phenylenediamine, N-($\beta$-methoxyethyl)-para-phenylenediamine, 4-N-[$\beta$-($\beta'$-hydroxyethoxy)-ethyl]-aminoaniline, 4-N,N-di-($\beta$-hydroxyethyl)-aminoaniline and 4-N-ethyl-N-carbamylmethyl-aminoaniline and salts thereof.

They can also contain para-aminophenols, for example: para-aminophenol, N-methyl-para-aminophenol, 2-chloro-4-aminophenol, 3-chloro-4-aminophenol and 2-methyl-4-aminophenol and salts thereof.

They can also contain heterocyclic derivatives, for example: 2,5-diaminopyridine and 7-aminobenzomorpholine.

Amongst the dyestuff precursors of the ortho type, there may be mentioned ortho-phenylenediamines, ortho-aminophenols and pyrocatechols, optionally containing substituents on the nucleus or on one of the amine groups.

The compositions according to the invention can contain, in association with the dyestuff precursors of the ortho or para type, couplers which are well known in the state of the art.

Couplers which may be mentioned in particular are: meta-diphenols such as: resorcinol, 2-methylresorcinol and 5-methylresorcinol; meta-aminophenols such as: meta-aminophenol, 2-methyl-5-aminophenol, 2-methyl-5-N-($\beta$-hydroxyethyl)-aminophenol, 2-methyl-5-N-($\beta$-mesylaminoethyl)-aminophenol, 2,6-dimethyl-3-aminophenol and 6-hydroxybenzomorpholine and their salts; meta-phenylenediamines such as: 2,4-diaminoanisole, 2,4-diaminophenoxyethanol, 6-aminobenzomorpholine and 2-N-($\beta$-hydroxyethyl)-amino-4-aminophenoxyethanol and their salts; and meta-acylaminophenols, meta-ureidophenols and meta-carbalkoxyaminophenols such as: 2-methyl-5-acetylaminophenol, 2,6-dimethyl-5-acetylaminophenol, 2-methyl-5-ureidophenol and 2-methyl-5-carbethoxyaminophenol.

Other couplers which can be used in the compositions of the invention include: $\alpha$-naphthol, couplers possessing an active methylene group, such as diketone compounds and pyrazolones, and heterocyclic couplers such as 2,4-diaminopyridine, and also their salts.

Other oxidation dyestuff precursors, which can be present in the compositions of the invention include leuco derivatives of indoanilines, of indamines and/or of indophenols, for example: 4,4'-dihydroxy-2-amino-5-methyldiphenylamine, 2-amino-4-hydroxy-5-methyl-4'-N,N-($\beta$-hydroxyethyl)-aminodiphenylamine and 2,4-dihydroxy-5-methyl-4'-N-($\beta$-methoxyethyl)-aminodiphenylamine dihydrochloride.

Other hair colouration precursors, which can be present include precursors of the benzene series contain-at least three nuclear hydroxy, methoxy and/or amino substituents, such as: 2,6-diaminohydroquinone dihydrochloride, 2,6-diamino-4-N,N-diethylaminophenol trihydrochloride, 2,4-diaminophenol dihydrochloride, 1,2,4-trihydroxybenzene, 2,3,5-trihydroxytoluene or 4-methoxy-2-amino-N-($\beta$-hydroxyethyl)-aniline.

Preferably, antioxidants such as sodium sulphite, thioglycolic acid, sodium bisulphite, ascorbic acid and hydroquinone are added to the compositions according to the invention which comprise oxidation dyestuff precursors. These antioxidants are advantageously present in proportions of 0.05 to 1.5% by weight, relative to the total weight of the composition.

The oxidation dyestuff precursors of the "para" or "ortho" type are suitably used in the compositions of the invention at concentrations of 0.001 to 5% by weight and preferably 0.03 to 2%, based on the total weight of the composition. The couplers are suitably used at concentrations of 0.001 to 5% by weight and preferably 0.015 to 2% by weight.

According to a first embodiment, the hair-dyeing process according to the invention, which involves development using an oxidising agent, consists in applying, to the hair, the dyeing composition comprising both direct dyestuff and dyestuff precursor, and in developing the colouration with the aid of an oxidizing agent which is present in the dyeing composition or is applied to the hair in a second stage.

The oxidizing agent is preferably hydrogen peroxide, urea peroxide or a per-salt. It is preferred to use a solution of hydrogen peroxide of 20 volumes strength.

According to another embodiment of the dyeing process according to the invention, which involves development using an oxidizing agent, a solution containing at least one direct dyestuff of formula (I), optionally in association with one or more other direct dyestuffs, is mixed at the time of use with a solution containing at least one dyestuff precursor but not containing any direct dyestuff, and the colouration is developed with the aid of an oxidising agent, which is added to the mixture or is applied to the hair in a second stage.

Once the oxidising agent has been applied to the hair, it is left on the hair for, say, 10 to 40 minutes, preferably 15 to 30 minutes, after which the hair is rinsed, shampooed and rinsed again, if appropriate, and dried.

The present invention is further illustrated in the following Examples.

EXAMPLE 1

Preparation of 3-amino-4-nitrophenyl $\beta,\gamma$-dihydroxypropyl ether 0.1 mol (17.3 g) of 3-amino-4-nitro-chlorobenzene, which is a known compound [Bios Final Report, 1,147 (1948)], is introduced gradually, at about 120° C., whilst stirring, into 2.4 mols (225 g) of glycerol in which 8.6 g of sodium hydroxide have been dissolved beforehand at about 120° C. When the addition has ended, heating is continued for 2½ hours and the reaction medium is then poured into 250 g of iced water. The desired product is extracted with ethyl acetate and the ethyl acetate is driven off in vacuo to give 13.6 g of crystalline product. After two recrystallisations from acetonitrile and drying in vacuo, 3-amino-4-nitrophenyl $\beta,\gamma$-dihydroxypropyl ether, which melts at 139° C., is collected.

| Analysis | Calculated for $C_9H_{12}N_2O_5$ | Found |
|---|---|---|
| C % | 47.37 | 47.28 |
| H % | 5.30 | 5.32 |
| N % | 12.28 | 12.22 |
| O % | 35.06 | 34.95 |

EXAMPLE 2

Preparation of 3-N-methylamino-4-nitrophenyl $\beta,\gamma$-dihydroxypropyl ether 0.268 mol (50 g) of 3-N-methylamino-4-nitrochlorobenzene, which is a known compound (Korner: Gazetta Chimica Italiana 4, 376), is introduced gradually, at about 120° C., whilst stirring, into 3.26 mols (300 g) of glycerol in which 11 g of sodium hydroxide have been dissolved beforehand at about 120° C. When the addition has ended, the reaction medium is kept at 120° C. for two hours, whilst stirring. 6 g of sodium hydroxide are then added and heating is continued for a further 1 hour 30 minutes. The reaction medium is poured into 300 g of ice water. The desired product is then extracted with ethyl acetate and the ethyl acetate is driven off in vacuo. The oily residue crystallises. After recrystallisation from isopropanol and then from dichloroethane and drying in vacuo, it melts at 94° C.

| Analysis | Calculated for $C_{10}H_{14}N_2O_5$ | Found | |
|---|---|---|---|
| C % | 49.58 | 49.59 | |
| H % | 5.83 | 5.82 | |
| N % | 11.57 | 11.37 | |
| O % | 33.03 | 32.94 | 32.83 |

EXAMPLE 3

Preparation of
3-N-(β-hydroxyethyl)-amino-4-nitrophenyl
β,γ-dihydroxypropyl ether 0.023 mol (5 g) of 3-N-(β-hydroxyethyl)-amino-4-nitro-chlorobenzene, which is a known compound [P. Clarke, J.C.S. 4,763, 7 (1963)], is introduced gradually, at about 125° C., whilst stirring, into 50 g of glycerol in which 1.85 g of sodium hydroxide have been dissolved beforehand at about 125° C. When the addition has ended, heating is continued for 3 hours at 125° C. and the reaction medium is then poured onto 80 g of crushed ice. After extraction of the desired product with ethyl acetate and removal of the solvent in vacuo, a crystalline residue is obtained which, after recrystallisation from isopropanol and drying in vacuo, melts at 91° C.

| Analysis | Calculated for $C_{11}H_{16}O_6N_2$ | Found |
|---|---|---|
| C % | 48.52 | 48.46 |
| H % | 5.92 | 5.95 |
| N % | 10.29 | 10.24 |

EXAMPLE 4

Preparation of 3-N-butylamino-4-nitrophenyl
β,γ-dihydroxypropyl ether

1st step: Preparation of 4-nitro-3-N-butylamino-chlorobenzene 0.2 mol (38.4 g) of 2,4-dichloro-nitrobenzene is heated under reflux for 2 hours in 150 ml of 96° strength ethanol and 150 ml of butylamine. After cooling to −5° C., the expected product crystallises. It is filtered off and washed with water and alcohol. After drying in vacuo and recrystallisation from alcohol, it melts at 38° C.

| Analysis | Calculated for $C_{10}H_{13}N_2O_2Cl$ | Found |
|---|---|---|
| C % | 52.52 | 52.58 |
| H % | 5.69 | 5.74 |
| N % | 12.25 | 12.24 |
| O % | 14.00 | 14.02 |
| Cl % | 15.54 | 15.60 |

2nd step: Preparation of 3-N-butylamino-4-nitrophenyl β,γ-dihydroxypropyl ether 0.1 mol (22.8 g) of 4-nitro-3-N-butylamino-chlorobenzene is added gradually, whilst stirring, to 200 g of glycerol to which 0.11 mol (4.4 g) of sodium hydroxide has been added and which has been heated to 120° C. beforehand. After heating for 2 hours at 120° C., 0.055 mol (2.2 g) of sodium hydroxide is added. Heating is continued for a further 5 hours and the cooled reaction medium is poured into 300 g of iced water and extracted with ethyl acetate. The ethyl acetate is driven off in vacuo.

After purification by chromatography on a silica column and recrystallisation from benzene, the residual product melts at 78° C.

| Analysis | Calculated for $C_{13}H_{20}N_2O_5$ | Found |
|---|---|---|
| C % | 54.93 | 54.94 |
| H % | 7.04 | 7.08 |
| N % | 9.86 | 9.85 |
| O % | 28.17 | 27.98 |

EXAMPLE 5

Preparation of
3-N-(β-hydroxypropyl)-amino-4-nitrophenyl
β,γ-dihydroxypropyl ether 1st step: Preparation of 4-nitro-3-N-(β-hydroxypropyl)amino-chlorobenzene.

0.208 mol (40 g) of 2,4-dichloro-nitrobenzene is added gradually, whilst stirring, to 80 ml of 1-propan-2-ol, heated to 70° C. beforehand, so as to keep the temperature between 75° and 80° C. When the addition has ended, heating is maintained for 1 hour at about 80° C. and the reaction medium is then poured into 250 g of 0.5 N hydrochloric acid. The expected product precipitates. It is filtered off, washed with water and recrystallised from 96° strength ethanol. After drying in vacuo, it melts at 110° C.

| Analysis | Calculated for $C_9H_{11}ClN_2O_3$ | Found |
|---|---|---|
| C % | 48.86 | 46.71 |
| H % | 4.81 | 4.79 |
| N % | 12.15 | 12.09 |
| O % | 20.81 | 20.90 |
| Cl % | 15.37 | 15.45 |

2nd step: Preparation of 3-N-(β-hydroxypropyl)-amino-4-nitrophenyl β,γ-dihydroxypropyl ether 0.06 mol (13.8 g) of 4-nitro-3-N-(β-hydroxypropyl)-amino-chlorobenzene is dissolved in 40 ml of glycerol at 130° C. 40 ml of glycerol, to which 2 ml of water and 0.062 mol (2.6 g) of sodium hydroxide has been added, are added gradually to this solution in the course of 2 hours, whilst stirring. Heating is maintained for a further 2 hours 30 minutes. The cooled reaction medium is poured into 500 ml of iced water and then extracted with ethyl acetate. The ethyl acetate is driven off in vacuo.

After purification by chromatography on silica and recrystallisation from acetonitrile, the residual product melts at 98° C.

| Analysis | Calculated for $C_{12}H_{18}N_2O_6$ | Found |
|---|---|---|
| C % | 50.34 | 50.25 |
| H % | 6.34 | 6.37 |
| N % | 9.79 | 9.71 |
| O % | 33.53 | 33.45 |

EXAMPLE 6

Direct dyeing

The following dyeing composition is prepared:

| | |
|---|---|
| 3-N—Butylamino-4-nitrophenyl β,γ-dihydroxypropyl ether | 0.5 g |
| 2-Butoxyethanol | 5 g |
| Lauryl alcohol containing 12 mols of ethylene oxide (per mol of alcohol) | 5 g |
| 22° B strength ammonia solution | 0.5 g |

The pH of this composition is equal to 9.

When applied for 30 minutes at 28° C. to hair which has been bleached white, this mixture imparts to the hair, after rinsing and shampooing, a light golden yellow colouration.

EXAMPLE 7

Direct dyeing

The following dyeing composition is prepared:

| | |
|---|---|
| 3-N—(β-hydroxypropyl)-amino-4-nitrophenyl β,γ-dihydroxypropyl ether | 0.5 g |
| 2-Butoxyethanol | 5 g |
| Lauryl alcohol containing 12 mols of ethylene oxide | 5 g |
| 22° B strength ammonia solution | 0.75 g |
| Water q.s.p. | 100 g |

The pH of this solution is equal to 9.5.

When applied for 30 minutes at 25° C. to hair which has been bleached white, this mixture imparts to the hair, after rinsing and shampooing, a laburnam-yellow colouration.

EXAMPLE 8

Direct dyeing

The following dyeing composition is prepared:

| | |
|---|---|
| 3-N—Methylamino-4-nitrophenyl β,γ-dihydroxypropyl ether | 1.5 g |
| 96° strength alcohol | 10 g |
| Diethanolamides of copra fatty acids | 2.2 g |
| Lauric acid | 0.8 g |
| Ethylene glycol monoethyl ether | 2 g |
| Monoethanolamine q.s.p. | pH 7.5 |
| Water q.s.p. | 100 g |

When applied for 20 minutes at 25° C. to hair which has been bleached white, this mixture imparts to the hair, after rinsing and shampooing, a gorse-yellow colouration.

EXAMPLE 9

Direct dyeing

The following dyeing composition is prepared:

| | |
|---|---|
| 3-N—(β-Hydroxyethyl)-amino-4-nitro-phenyl β,γ-dihydroxypropyl ether | 0.73 g |
| 2-Butoxyethanol | 10 g |
| Carbopol 934 | 2 g |
| Monoethanolamine q.s.p. | pH 5.5 |
| Water q.s.p. | 100 g |

When applied for 40 minutes at 28° C. to hair which has been bleached white, this mixture imparts to the hair, after rinsing and shampooing, a vivid yellow colouration.

EXAMPLE 10

Direct dyeing

The following dyeing composition is prepared:

| | |
|---|---|
| 3-N—(β-Hydroxyethyl)-amino-4-nitro- | 0.06 g |
| 2-Butoxyethanol | 10 g |
| Carbopol 934 | 2 g |
| 20% strength aqueous solution of monoethanolamine | 10 g |
| Water q.s.p. | 100 g |

The pH of this composition is equal to 10.

When applied for 30 minutes at 30° C. to hair which has been bleached white, the mixture imparts to the hair, after rinsing and shampooing, a golden honey colouration.

EXAMPLE 11

Direct dyeing

The following composition is prepared:

| | |
|---|---|
| 3-N—Methylamino-4-nitrophenyl β,γ-dihydroxypropyl ether | 0.05 g |
| 3-Nitro-4-N'—methylamino-N—(β-aminoethyl)-aniline dihydrobromide | 0.035 g |
| 96° strength alcohol | 5 g |
| Carbopol 934 | 2 g |
| Triethanolamine q.s.p. | pH 8.8 |
| Water q.s.p. | 100 g |

When applied to bleached hair for 30 minutes at 28° C., this mixture imparts to the hair, a golden sandy colouration with a slight pink sheen

EXAMPLE 12

Direct dyeing

The following dyeing composition is prepared:

| | |
|---|---|
| 3-N—(β-Hydroxyethyl)-amino-4-nitro-phenyl β,γ-dihydroxypropyl ether | 0.215 g |
| 3-Nitro-4-N—(β-hydroxyethyl)-amino 6-chloroaniline | 0.18 g |
| Juglone | 0.42 g |
| 2-Butoxyethanol | 15 g |
| 20% strength aqueous solution of triethanolamine | 10 g |
| Water q.s.p. | 100 g |

This composition has a pH of 8.5.

When applied for 25 minutes at 30° C. to hair which has been bleached white, this composition imparts to the hair, after rinsing and shampooing, a very light mahogany colouration.

EXAMPLE 13

Direct dyeing

The following dyeing composition is prepared:

| | |
|---|---|
| 3-N—Methylamino-4-nitrophenyl β,γ-dihydroxypropyl ether | 1.13 g |
| 3-Nitro-4-N—(β-hydroxyethyl)-amino-6-chloroaniline | 0.38 g |
| Tetraaminoanthraquinone | 0.1 g |
| 2-Butoxyethanol | 10 g |
| 96° strength alcohol | 5 g |
| Cemulsol NP4 | 12 g |
| Cemulsol NP9 | 15 g |
| Oleyl alcohol oxyethyleneated with 2 mols of ethylene oxide | 1.5 g |
| Oleyl alcohol exyethyleneated with 4 mols of ethylene oxide | 1.5 g |
| Monoethanolamine q.s.p. | pH 10.8 |

-continued

| | |
|---|---|
| Water q.s.p. | 100 g |

When applied for 30 minutes at 28° C. to hair which has been bleached white, this mixture imparts to the hair, after rinsing and shampooing, a light golden coppery colouration.

EXAMPLE 14

Direct dyeing

The following dyeing composition is prepared:

| | |
|---|---|
| 3-N—Methylamino-4-nitrophenyl β,γ-dihydroxypropyl ether | 0.15 g |
| 3-Nitro-4-aminophenol | 0.155 g |
| 2-N—(β-Hydroxyethyl)-amino-5-[4'-di-(β-hydroxyethyl)-aminoanilino] 1,4-benzoquinone | 0.15 g |
| 3-Nitro-4-N'—methylamino-N—(β-aminoethyl)-aniline dihydrobromide | 0.76 g |
| 96° strength alcohol | 5 g |
| Alfol C$_{16}$/$_{18}$E | 8 g |
| Lanette wax E | 0.5 g |
| Cemulsol B | 1 g |
| Oleyl diethanolamide | 1.5 g |
| Monoethanolamine q.s.p. | pH 9.3 |
| Water q.s.p. | 100 g |

When applied for 30 minutes to hair which has been bleached straw yellow beforehand, this mixture imparts to the hair, after rinsing and shampooing, a mahogany colouration.

EXAMPLE 15

Direct dyeing

The following dyeing composition is prepared:

| | |
|---|---|
| 3-N—Methylamino-4-nitrophenyl β,γ-dihydroxypropyl ether | 0.06 g |
| 2-Methyl-4-amino-5-nitrophenyl | 0.8 g |
| 3-Nitro-4-N'—Methylamino-N—(β-aminoethyl)-aniline dihydrobromide | 0.76 g |
| Alfol C$_{16}$/$_{18}$E | 8 g |
| Lanette wax E | 0.5 g |
| Cemulsol B | 1 g |
| Oleyl diethanolamide | 1.5 g |
| Masquol | 2.5 g |
| 22° B strength ammonia solution | 10 g |
| Water q.s.p. | 100 g |

This composition has a pH of 10.3.

When applied to 90% naturally white hair at 20°–25° C., this mixture imparts to the hair, after rinsing and shampooing, a coppery-red colouration.

EXAMPLE 16

Direct dyeing

The following dyeing composition is prepared:

| | |
|---|---|
| 3-N—Methylamino-4-nitrophenyl β,γ-dihydroxypropyl ether | 0.107 g |
| 2-Methyl-4-amino-5-nitrophenol | 0.105 g |
| Tetraaminoanthraquinone | 0.122 g |
| 2-Amino-4-methyl-6-nitrophenol | 0.4 g |
| Tween 80 | 12 g |
| Oleic acid | 20 g |
| Triethanolamine q.s.p. | pH 9.3 |
| Water q.s.p. | 100 g |

When applied for 25 minutes at 28° C. to hair which has been bleached white, this mixture imparts to the hair, after rinsing and shampooing, a coppery light blond colouration.

EXAMPLE 17

Direct dyeing

The following dyeing composition is prepared:

| | |
|---|---|
| 3-N—(β-Hydroxyethyl)-amino-4-nitrophenyl β,γ-dihydroxypropyl ether | 0.08 g |
| 3-Nitro-4-N—(β-hydroxyethyl)-aminophenol | 0.16 g |
| Tetraaminoanthraquinone | 0.2 g |
| 2-N—(β-Hydroxyethyl)amino-5-[4'-di-(β-hydroxyethyl)-aminoanilino] 1,4-benzoquinone | 0.15 g |
| 96° strength ethanol | 10 g |
| Cemulsol NP$_4$ | 12 g |
| Cemulsol NP$_9$ | 15 g |
| Oleyl alcohol oxyethyleneated with 2 mols of ethylene oxide | 1.5 g |
| Oleyl alcohol oxyethyleneated with 4 mols of ethylene oxide | 1.5 g |
| 20% strength aqueous solution of triethanolamine | 2 g |
| Water q.s.p. | 100 g |

This composition has a pH of 9.

When applied for 30 minutes at 28° C. to hair which has been bleached white, this mixture imparts to the hair, after rinsing and shampooing, a pink champagne colouration.

EXAMPLE 18

Wavesetting lotion

The following wavesetting lotion is prepared:

| | |
|---|---|
| 3-N—(β-Hydroxyethyl)-amino-4-nitrophenyl β,γ-dihydroxypropyl ether | 0.048 g |
| 2-[4'-(N—Ethyl-N—Carbamylmethyl) amino-phenyl]-methyl-5-ureidobenzoquinone-imine | 0.057 g |
| 2-(4'-N—Methylamino-3'-chlorophenyl)-methyl-5-ureidobenzoquinone-imine | 0.042 g |
| 30% vinylpyrrolidone/70% vinyl acetate copolymer E 335 sold by General Aniline and Film Corporation | 2 g |
| Ethanol | 40 g |
| 20% strength aqueous solution of triethanolamine | 3 g |
| Water q.s.p. | 100 g |

This composition has a pH of 8.

When applied as a wavesetting lotion to hair which has been bleached white, this mixture imparts to the hair, after drying, a dove grey colouration.

EXAMPLE 19

Wavesetting lotion

The following wavesetting lotion is prepared:

| | |
|---|---|
| 3-Amino-4-nitrophenyl β,γ-dihydroxypropyl ether | 0.102 g |
| 2-(4'-N—Methylamino-3'-chlorophenyl)-methyl-5-ureidobenzoquinone-imine | 0.042 g |
| 90% vinyl acetate/10% crotonic acid copolymer | 2 g |
| 96° strength ethanol | 50 g |
| 20% strength aqueous solution of triethanolamine | 3 g |

-continued

| | |
|---|---|
| Water q.s.p. | 100 g |

This solution has a pH of 7.

When applied to bleached hair as a wavesetting lotion, this composition imparts to the hair, after drying, a pearlescent pink beige colouration.

EXAMPLE 20

Oxidation dyeing

The following dyeing composition is prepared:

| | |
|---|---|
| Para-phenylenediamine | 0.21 g |
| Para-aminophenol | 0.6 g |
| Resorcinol | 0.705 g |
| Meta-aminophenol | 0.06 g |
| 2-Methyl-5-N—($\beta$-hydroxyethyl)-amino phenol | 0.33 g |
| 2,4-Diaminophenoxyethanol dihydrochloride | 0.23 g |
| 3-N—Methylamino-4-nitrophenyl $\beta,\gamma$-dihydroxypropyl ether | 1 g |
| 2-Amino-3-nitrophenol | 0.51 g |
| Cemulsol NP$_4$ | 12 g |
| Cemulsol NP$_9$ | 15 g |
| Oleyl alcohol containing 2 mols of ethylene oxide | 1.5 g |
| Oleyl alcohol containing 4 mols of ethylene oxide | 1.5 g |
| Propylene glycol | 6 g |
| Trilon B | 0.12 g |
| Thioglycolic acid | 0.6 g |
| 22° B strength ammonia solution | 11 g |
| Water q.s.p. | 100 g |

100 g of hydrogen peroxide of 20 volumes strength are added at the time of use. When applied to 90% naturally white hair for 30 minutes at 25°, this mixture imparts to the hair, after rinsing and shampooing, a golden medium chestnut colouration.

EXAMPLE 21

Oxidation dyeing

The following dyeing composition is prepared:

| | |
|---|---|
| 4-N,N—Di-($\beta$-hydroxyethyl)-amino-aniline dihydrochloride | 0.134 g |
| Para-aminophenol | 0.21 g |
| N—Methyl-para-aminophenol | 0.11 g |
| 2-Methyl-5-N—($\beta$-hydroxyethyl)-aminophenol | 0.38 g |
| Resorcinol | 0.105 g |
| 3-N—Methylamino-4-nitrophenyl $\beta,\gamma$-dihydroxypropyl ether | 0.304 g |
| Carboxymethylcellulose | 2 g |
| Ammonium lauryl-sulphate | 5 g |
| Ammonium acetate | 1 g |
| Propylene glycol | 8 g |
| 2-Butoxyethanol | 8 g |
| Masquol DTPA | 2 g |
| Thioglycolic acid | 0.4 g |
| 22° B strength ammonia solution | 10 g |
| Water q.s.p. | 100 g |

This composition has a pH of 10.3.

80 g of hydrogen peroxide of 20 volumes strength are added at the time of use.

When applied to 90% naturally white hair for 30 minutes at 28° C., this mixture imparts to the hair, after rinsing and shampooing, a golden copper colouration.

EXAMPLE 22

Oxidation dyeing

Two solutions (A) and (B) are prepared.

| | |
|---|---|
| Solution A | |
| 3-N—($\beta$-Hydroxyethyl)-amino-4-nitrophenyl $\beta,\gamma$-dihydroxypropyl ether | 0.53 g |
| 2-Methyl-5-amino-6-nitrophenol | 0.15 g |
| 3-Nitro-4-N—($\beta$-hydroxyethyl)-amino-6-chloroaniline | 0.135 g |
| 2-Butoxyethanol | 10 g |
| Solution B | |
| 4-N,N—Di-($\beta$hydroxyethyl)-amino-aniline dihydrochloride | 0.188 g |
| Para-aminophenol | 0.615 g |
| Resorcinol | 0.47 g |
| Meta-aminophenol | 0.2 g |
| 2-Methyl-5-N—($\beta$-hydroxyethyl)-amino-phenol | 0.12 g |
| Cemulsol NP$_4$ | 12 g |
| Cemulsol NP$_9$ | 15 g |
| Oleyl alcohol containing 2 mols of ethylene oxide | 1.5 g |
| Oleyl alcohol containing 4 mols of ethylene oxide | 1.5 g |
| Propylene glycol | 6 g |
| Trilon B | 0.12 g |
| 22° B strength ammonia solution | 11 g |
| Thioglycolic acid | 0.6 g |
| Water q.s.p. | 100 g |

Solution (A) is added to solution (B) at the time of use. 100 g of hydrogen peroxide of 20 volumes strength are added to the mixture, which has a pH of 10.4.

When applied to 90% naturally white hair for 25 minutes at 28° C., this mixture imparts to the hair, after rinsing and shampooing, a very golden, light chestnut colouration.

Details of the various tradenames and Registered Trade Marks used in the preceding Examples are given below:

CARBOPOL 934: Acrylic acid polymer of molecular weight 2 to 3 million, sold by Goodrich Chemical Company.

CEMULSOL NP$_4$: Nonylphenol containing 4 mols of ethylene oxide, sold by Rhone Poulenc.

CEMULSOL NP$_9$: Nonylphenol containing 9 mols of ethylene oxide, sold by Rhone Poulenc.

ALFOL C$_{16/18}$E (50/50): Cetyl/stearyl alcohol sold by Condea.

Lanette Wax E: Partially sulphated cetyl/stearyl alcohol sold by Henkel.

CEMULSOL B: Oxyethyleneated castor oil sold by Rhone Poulenc.

TWEEN 80: Polyoxyethyleneated sorbitol monooleate.

TRILON B: Sodium salt of ethylenediaminetetraacetic acid.

MASQUOL: Sodium salt of diethylenetriaminepentaacetic acid.

We claim:

1. A compound having the formula:

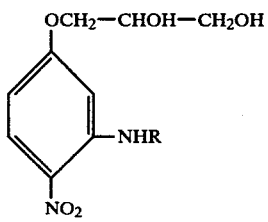

in which R denotes hydrogen, a lower alkyl, lower hydroxyalkyl or lower polyhydroxyalkyl radical.

2. A compound according to claim 1, in which R denotes a $C_1$ to $C_4$ alkyl radical, a $C_2$ to $C_6$ hydroxyalkyl radical or, a $C_3$ to $C_6$ polyhydroxyalkyl radical.

3. A compound according to claim 1, which is 3-amino-4-nitrophenyl $\beta,\gamma$-dihydroxypropyl ether.

4. A compound according to claim 1, which is 3-N-methylamino-4-nitrophenyl $\beta,\gamma$-dihydroxypropyl ether.

5. A compound according to claim 1, which is 3-N-butylamino-4-nitrophenyl $\beta,\gamma$-dihydroxypropyl ether.

6. A compound according to claim 1, which is 3-N-($\beta$-hydroxyethyl)-amino-4-nitrophenyl $\beta,\gamma$-dihydroxypropyl ether.

7. A compound according to claim 1, which is 3-N-($\beta$-hydroxypropyl)-amino-4-nitrophenyl $\beta,\gamma$-dihydroxypropyl ether.

8. A compound according to claim 1, which is 3-N-($\beta,\gamma$-dihydroxypropyl)-amino-4-nitrophenyl $\beta,\gamma$-dihydroxypropyl ether.

9. Process for the preparation of a compound as defined in claim 1, which comprises reacting 3-amino-4-nitro-chlorobenzene or a derivative thereof, of the formula:

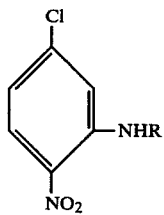

in which R is as defined in claim 1, with glycerol, in the presence of sodium hydroxide, at a temperature of 100° to 150° C.

10. A composition suitable for dyeing human hair which comprises an aqueous, alcoholic or aqueous-alcoholic vehicle and an effective amount of at least one compound as defined in claim 1.

11. A composition according to claim 10, which contains 0.001 to 5% by weight of at least one said compound relative to the total weight of the composition.

12. A composition according to claim 11, which contains 0.01 to 3% by weight of said compound relative to the total weight of the composition.

13. A composition according to claim 10, which also comprises any other direct dyestuff which is an azo or anthraquinone dyestuff, a nitrobenzene dyestuff or an indoaniline, indophenol, indamine, or hydroxynaphthoquinone, at a concentration of 0.001 to 5% by weight.

14. A composition according to claim 10, which has a pH of 3 to 11.5.

15. A composition according to claim 14, which has a pH of 5 to 11.5.

16. A composition according to claim 10, which also contains an anionic, cationic, non-ionic or amphoteric surface-active agent or a mixture thereof, at a concentration of 0.5 to 55% by weight.

17. A composition according to claim 16, which contains said surface-active agent at a concentration of 4 to 40% by weight, relative to the total weight of the composition.

18. A composition according to claim 10, which also contains organic solvent at a concentration from 1 to 75% by weight, relative to the total weight of the composition.

19. A composition according to claim 18, which contains said organic solvent at a concentration of 5 to 50% by weight, relative to the total weight of the composition.

20. A composition according to claim 10, which also contains thickener at a concentration of 0.5 to 10% by weight, relative to the total weight of the composition.

21. A composition according to claim 20, which contains said thickener at a concentration of 0.5 to 3% by weight, relative to the total weight of the composition.

22. A composition according to claim 10, which also contains at least one cosmetic resin at a concentration of 1 to 3% by weight, relative to the total weight of the composition.

23. A composition according to claim 22, which contains 1 to 2% of said cosmetic resin, relative to the total weight of the composition.

24. A composition according to claim 10, which also contains at least one ortho or para oxidation dyestuff precursor or a mixture thereof, at a concentration of 0.001 to 5% by weight.

25. A composition according to claim 24, which contains 0.03 to 2% by weight of the precursor.

26. A composition according to claim 24, in which the precursor is selected from the group consisting of a para-phenylenediamine, para-aminophenol, ortho-phenylenediamine, ortho-aminophenol, pyrocatechol, a salt thereof and a heterocyclic derivative.

27. A composition according to claim 24, which also contains, as coupler, a meta-diphenol, meta-aminophenol, meta-phenylenediamine, meta-acylaminophenol, meta-ureidophenol, meta-carbalkoxyaminophenol, $\alpha$-naphthol, a heterocyclic coupler, a pyrazolone or diketone, or a salt thereof, at a concentration of 0.001 to 5% by weight.

28. A composition according to claim 27, which contains 0.015 to 2% by weight of the coupler.

29. A composition according to claim 24, which also contains an antioxidant at a concentration of 0.05 to 1.5% by weight, relative to the total weight of the composition.

30. Process for the direct dyeing of human hair, which comprises applying thereto an effective amount of a composition as defined in claim 10, leaving it on the hair for 5 to 40 minutes and then rinsing, washing, if desired, and drying the hair.

31. Process for dyeing human hair, which comprises applying to hair which has been washed and rinsed before hand, an effective amount of a dyeing composition as defined in claim 22 and then winding the hair onto rollers and drying it.

32. Process for the oxidation dyeing of human hair, which comprises applying thereto an effective amount of a composition as defined in claim 24, the colouration being developed with an oxidising agent which is present in the said composition or is subsequently applied to the hair.

33. Process for the oxidation dyeing of human hair, which comprises mixing a composition as defined in claim 10 at the time of use with a dyeing composition containing at least one oxidation dyestuff precursor but not containing any direct dyestuff, and applying the mixture to the hair, the colouration being developed with an oxidising agent which is added to the mixture or is subsequently applied to the hair.

34. Process according to claim 32, in which the dyeing composition or the mixture of dyeing compositions and the oxidising agent are left on the hair for 10 to 40 minutes, and then rinsing, shampooing and rinsing again, if desired, and drying the hair.

35. Process according to claim 33, in which the dyeing composition or the mixture of dyeing compositions and the oxidising agents are left on the hair for 10 to 40 minutes, and then rinsing, shampooing and rinsing again, if desired, and drying the hair.

* * * * *